United States Patent
Ophardt (10) Patent No.: US 10,878,275 B2
(45) Date of Patent: Dec. 29, 2020

(54) GLOVE SENSING DISPENSER

(71) Applicant: OP-Hygiene IP GmbH, Niederbipp (CH)

(72) Inventor: Heiner Ophardt, Arisdorf (CH)

(73) Assignee: OP-Hygiene IP GmbH, Niederbipp (CH)

( * ) Notice: Subject to any disclaimer, the term of this patent is extended or adjusted under 35 U.S.C. 154(b) by 0 days.

(21) Appl. No.: 16/373,130

(22) Filed: Apr. 2, 2019

(65) Prior Publication Data
US 2020/0320330 A1    Oct. 8, 2020

(51) Int. Cl.
*G06K 9/46*     (2006.01)
*A47K 5/12*     (2006.01)

(52) U.S. Cl.
CPC .......... *G06K 9/4604* (2013.01); *A47K 5/1202* (2013.01); *A47K 5/1217* (2013.01)

(58) Field of Classification Search
CPC ... G06K 9/4604; A47K 5/1202; A47K 5/1217
See application file for complete search history.

(56) References Cited

U.S. PATENT DOCUMENTS

| | | | |
|---|---|---|---|
| 8,245,877 B2 | 8/2012 | Ophardt | |
| 8,397,949 B2 | 3/2013 | Ophardt | |
| 9,122,332 B2 | 9/2015 | Li et al. | |
| 9,204,823 B2 | 12/2015 | Derenne et al. | |
| 9,671,894 B2 | 6/2017 | Schenkewitz | |
| 9,785,744 B2 | 10/2017 | Johnson et al. | |
| 2011/0169646 A1* | 7/2011 | Raichman | G08B 21/245 340/573.1 |
| 2011/0303695 A1 | 12/2011 | Fern | |
| 2014/0327545 A1 | 11/2014 | Bolling et al. | |
| 2016/0339132 A1* | 11/2016 | Cosman | A61L 2/0088 |
| 2017/0076042 A1 | 3/2017 | Katz et al. | |
| 2017/0246331 A1* | 8/2017 | Lloyd | A61L 2/084 |
| 2019/0043337 A1* | 2/2019 | Liu | G16H 40/20 |

FOREIGN PATENT DOCUMENTS

| | | |
|---|---|---|
| WO | 2011123741 A2 | 10/2011 |
| WO | 2019106078 | 6/2019 |

OTHER PUBLICATIONS

Scheithauer et al., "Disinfection of gloves: feasible, but pay attention to the disinfectant/glove combination" Journal of Hospital Infection 94 (2016) 268-272.
Ophardt Hygiene Complete Catalogue (2017) p. 42, 43, 48, 49.
Berkeley Sensor & Actuator Center, "Existing Ultrasonic Transducers" (Apr. 2017) p. 9.

* cited by examiner

*Primary Examiner* — Chad G Erdman
(74) *Attorney, Agent, or Firm* — Thorpe North & Western, LLP

(57) ABSTRACT

A fluid dispenser having a pump mechanism that, when activated, dispenses an allotment of fluid onto a user's hand. The fluid dispenser includes a sensor that senses a property of the user's hand, and a processor that determines, based on the property of the user's hand, whether the user's hand is wearing a glove.

20 Claims, 5 Drawing Sheets

Fig. 5

GLOVE SENSING DISPENSER

FIELD OF THE INVENTION

This invention relates to hand cleaning fluid dispensers, and more particularly to dispensers that have a sensor that senses a user's hand.

BACKGROUND OF THE INVENTION

Hand cleaning fluid dispensers that sense when a user's hand is placed under or near the dispenser are known in the art. For example, many known dispensers include a proximity sensor that detects when a user's hand is positioned to receive hand cleaning fluid from the dispenser, which triggers the activation of a pump mechanism to dispense an allotment of fluid onto the user's hand. This allows the dispenser to operate touchlessly.

Typically, known hand cleaning fluid dispensers are intended to dispense fluid directly onto a user's bare hands, to sanitize or disinfect the outer surface of the user's skin. However, the practice of dispensing cleaning fluid directly onto gloves, such as medical or surgical gloves, to sanitize or disinfect the outer surface of the gloves, is becoming a common practice. In some circumstances, such as where hand disinfection is required in rapid succession during the treatment of a single patient, this practice may improve workflow and hygiene compliance rates.

The applicant has appreciated a disadvantage of the prior art is that, in known hand cleaning fluid dispensers, the sensor which senses the user's hand does not determine whether or not the user's hand is wearing a glove. The applicant has appreciated a further disadvantage of the prior art is that known dispensers are operated in the same manner, whether or not the user's hand is wearing a glove.

SUMMARY OF THE INVENTION

To at least partially overcome some of the disadvantages of previously known methods and devices, the present invention provides a fluid dispenser for dispensing fluid onto a user's hand, and a sensor that senses a property of an external surface presented by the user's hand, the property of the external surface presented by the user's hand being used to determine whether the user's hand is wearing a glove. The inventors have appreciated that having the dispenser determine whether the user's hand is wearing a glove allows the dispenser to provide improved functionality. For example, the operation of the dispenser can be controlled based on whether or not the user's hand is determined to be wearing a glove. The dispenser can, for example, be configured to automatically adjust a characteristic of the allotment of fluid, such as volume and/or composition, based on whether the user's hand is wearing a glove. The applicant has appreciated that, generally, less fluid is needed to disinfect a gloved hand versus a non-gloved hand, because gloves typically have a smooth outer surface. In accordance with the present invention, the dispenser can thus automatically change the volume of fluid that is dispensed, preferably reducing the volume, when the user's hand is determined to be wearing a glove, and thus avoid dispensing more fluid than is needed.

Optionally, the dispenser can also be configured to adjust the composition of the allotment of fluid based on whether the user's hand is wearing a glove, as by adjusting the proportions of different fluids available to be dispensed. For example, the dispenser can incorporate two separate fluid reservoirs that each contain a different hand cleaning fluid, one of which is dispensed when the user's hand is determined to be wearing a glove, and the other of which is dispensed when the user's hand is determined to not be wearing a glove. This allows the composition of the hand cleaning fluid to be optimized based on the presence or absence of a glove on the user's hand. For example, in some circumstances it may be advantageous to dispense fluid containing a particular ingredient only when the user's hand is wearing a glove. This could occur, for example, if the ingredient is too harsh to be applied directly to the user's skin. In other circumstances, it may be advantageous to dispense fluid containing certain ingredients only when the user's hand is not wearing a glove. This could occur, for example, if the ingredients react with or degrade the material from which the gloves are made.

The dispenser can also be configured to record and/or transmit information indicative of whether the user's hand is wearing a glove. For example, the information can be transmitted to a hand cleaning compliance monitoring system, to track compliance with hand hygiene protocols. By incorporating the sensor directly into the hand cleaning fluid dispenser, the compliance monitoring system is able to collect accurate information about glove wearing with each activation of the dispenser, and the compliance data on glove wearing can be usefully linked to the compliance data on hand cleaning.

The inventors have appreciated that the presence or absence of a glove on the user's hand can be determined by measuring the surface temperature of the surface presented to a sensor by the user's hand, whether for example the surface is human skin when the hand is not gloved or the exterior surface of the glove when the hand is gloved, as the surface temperature will usually be lower when the hand is wearing a glove compared to when the user's hand is not wearing a glove. The sensor may, for example, be an infrared temperature sensor that detects whether the external surface presented by a user's hand is above or below a threshold temperature. If below the threshold temperature, the user's hand is considered to be wearing a glove, and if above the threshold temperature, the user's hand is considered to not be wearing a glove. The sensor may, for example, be an infrared temperature sensor that determines if the external surface presents a thermal image representative of blood vessels in a hand that would not be apparent if the hand is in a glove.

In other embodiments, the sensor could be an optical sensor that detects one or more optical features of the external surface presented by a user's hand to determine whether the user's hand is wearing a glove. For example, the optical sensor could detect the color of the external surface presented; the presence or absence of a predetermined visual feature on the external surface presented, such as a visual pattern; a reflective property of the external surface presented; and/or a light absorption property of the external surface presented.

The present invention also provides a hygiene station including a glove dispenser that dispenses gloves, and a fluid dispenser that, when activated, dispenses an allotment of fluid onto a user's hand. The hygiene station also includes a sensor that senses when one of the gloves has been dispensed, and a station monitoring system that records and/or transmits information indicative of when the gloves are dispensed and when the fluid dispenser is activated. The inventors have appreciated that the hygiene station can usefully collect information about glove wearing and hand cleaning, as well as the order and timing of glove and fluid dispensing events. This information can, for example, be transmitted to a hand cleaning compliance monitoring system, to track compliance with hand hygiene protocols.

Accordingly, in one aspect the present invention resides in a method comprising:

providing a fluid dispenser having a sensor that senses a property of an external surface presented by a user's hand, and a pump mechanism that, when activated, dispenses an allotment of fluid onto the user's hand;

using the sensor to sense the property of the external surface presented by the user's hand; and determining, based on the property of the external surface presented by the user's hand, whether the user's hand is wearing a glove.

The method optionally further comprises: controlling operation of the dispenser based on whether the user's hand is determined to be wearing a glove.

The method optionally further comprising adjusting a characteristic of the allotment of fluid based on whether the user's hand is determined to be wearing a glove.

The characteristic of the allotment of fluid that is adjusted based on whether the user's hand is determined to be wearing a glove may, for example, comprise at least one of:

(i) a volume of the allotment of fluid; and
(ii) a composition of the allotment of fluid.

In some embodiments, the volume of the allotment of fluid is decreased when the user's hand is determined to be wearing a glove.

Optionally, the fluid dispenser further comprises a data storage unit and/or a data transmission unit, the method further comprising at least one of:

using the data storage unit to record information indicative of whether the user's hand is determined to be wearing a glove; and using the data transmission unit to transmit information indicative of whether the user's hand is determined to be wearing a glove.

In some embodiments, the information indicative of whether the user's hand is determined to be wearing a glove is transmitted to a compliance monitoring system.

The sensor may, for example, comprise at least one of: a temperature sensor and an optical sensor.

In some preferred embodiments, the sensor comprises an infrared sensor that senses a temperature of the external surface presented by the user's hand, the method further comprising:

using the infrared sensor to sense whether the external surface presented by the user's hand is above or below a threshold temperature;

determining that the user's hand is wearing a glove if the temperature of the external surface presented by the user's hand is below the threshold temperature; and determining that the user's hand is not wearing a glove if the temperature of the external surface presented by the user's hand is above the threshold temperature.

Preferably, the fluid dispenser determines whether the user's hand is wearing a glove before the allotment of fluid is dispensed onto the user's hand; and wherein the fluid dispenser waits until at least one of:
(a) a predetermined time period has passed; and
(b) the user has moved away from the fluid dispenser;
before making a subsequent determination of whether the user's hand, or a subsequent user's hand, is wearing a glove.

In some embodiments, the sensor comprises the optical sensor, and the optical sensor detects at least one of:

a color of the external surface presented by the user's hand;

a presence or an absence of a predetermined visual feature on the external surface presented by the user's hand;

a reflective property of the external surface presented by the user's hand; and a light absorption property of the external surface presented by the user's hand.

Preferably, the fluid is a hand cleaning fluid, the method further comprising:

dispensing the allotment of fluid onto the user's hand.

In some embodiments, the fluid is a hand cleaning fluid; and the fluid dispenser further comprises a data transmission unit, the method further comprising:

dispensing the allotment of fluid onto the user's hand; and using the data transmission unit to transmit information indicative of whether the user's hand is determined to be wearing a glove to a compliance monitoring system.

Preferably, the sensor comprises an infrared sensor that senses a temperature of the external surface presented by the user's hand, the method further comprising:

using the infrared sensor to sense whether the external surface presented by the user's hand is above or below a threshold temperature;

determining that the user's hand is wearing a glove if the temperature of the external surface presented by the user's hand is below the threshold temperature; and determining that the user's hand is not wearing a glove if the temperature of the external surface presented by the user's hand is above the threshold temperature.

In another aspect, the present invention resides in a fluid dispenser comprising:

a pump mechanism that, when activated, dispenses an allotment of fluid onto a user's hand;

a sensor that senses a property of an external surface presented by the user's hand; and a processor that determines, based on the property of the external surface presented by the user's hand, whether the user's hand is wearing a glove.

Optionally, the fluid dispenser further comprises a fluid adjustment system that adjusts a characteristic of the allotment of fluid based on whether the user's hand is determined to be wearing a glove.

In some preferred embodiments, the fluid dispenser further comprises a data transmission unit that transmits information indicative of whether the user's hand is determined to be wearing a glove to a compliance monitoring system.

In a further aspect, the present invention resides in a hygiene station comprising:

a glove dispenser that dispenses gloves;

a fluid dispenser that, when activated, dispenses an allotment of fluid onto a user's hand;

a sensor that senses when one of the gloves has been dispensed; and a station monitoring system that records and/or transmits information indicative of when the gloves are dispensed and when the fluid dispenser is activated.

Preferably, each time one of the gloves is dispensed from the glove dispenser, the station monitoring system records and/or transmits information indicative of whether the fluid dispenser was activated within a predetermined time period immediately preceding the dispensing of the glove.

In some embodiments, the hygiene station further comprises a user sensor that senses when a user is positioned within a predetermined area adjacent to the hygiene station;

wherein the station monitoring system records and/or transmits information indicative of an order in which the gloves are dispensed and the fluid dispenser is activated over a time period in which the user is positioned within the predetermined area.

Optionally, the hygiene station further comprises a glove sensor that senses whether the user's hand is wearing a glove.

BRIEF DESCRIPTION OF THE DRAWINGS

Further aspects and advantages of the invention will appear from the following description taken together with the accompanying drawings, in which.

DETAILED DESCRIPTION OF THE DRAWINGS

Figure 1:
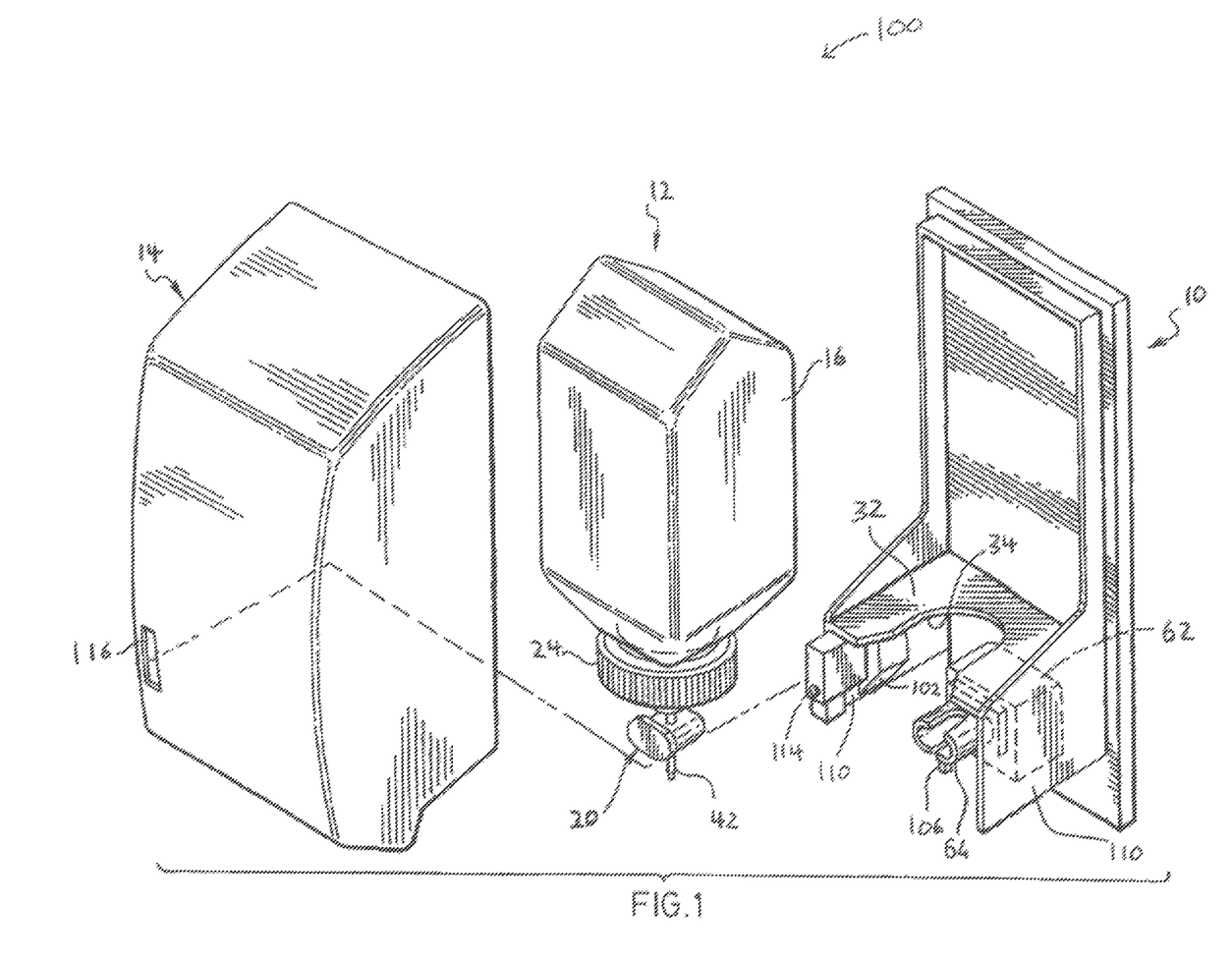
FIG. 1 is an exploded perspective view of a dispenser in accordance with a first embodiment of the present invention.
Figure 2:
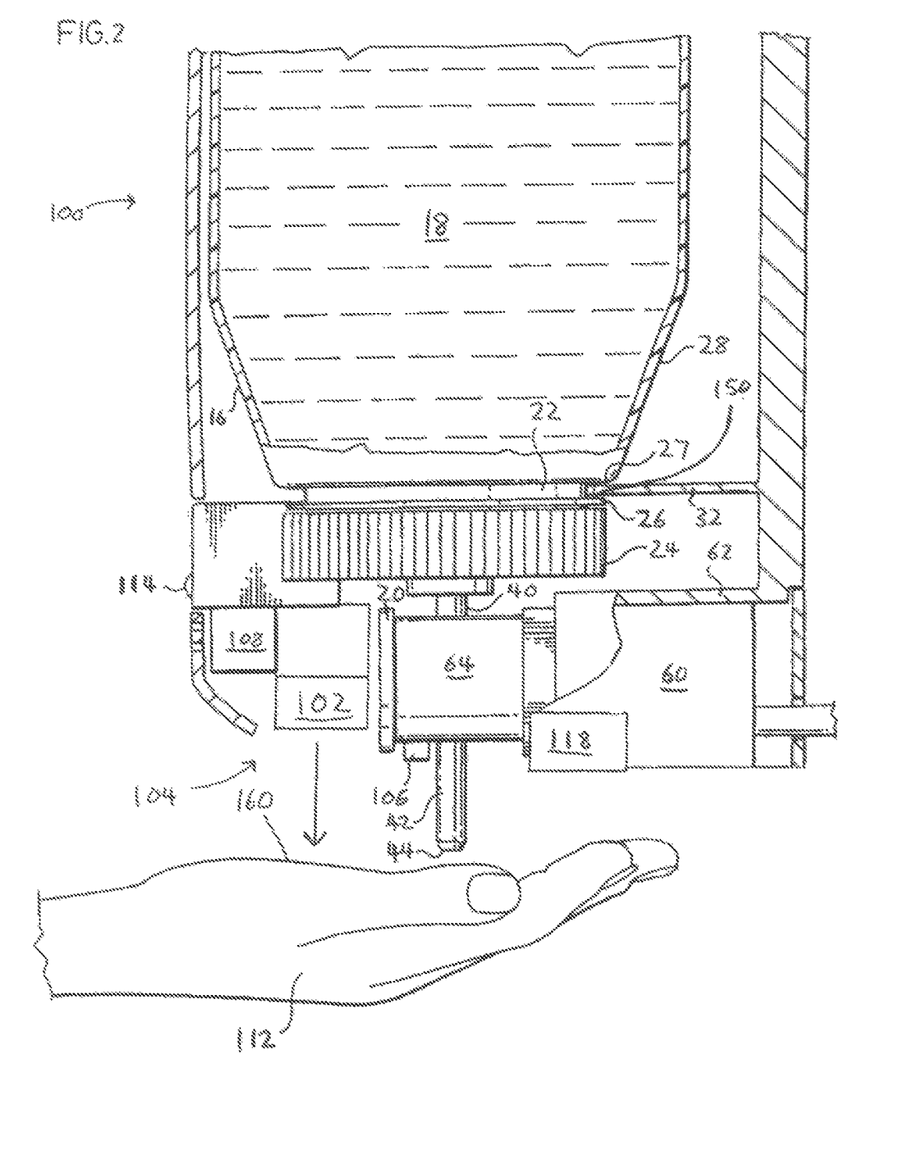
FIG. 2 is a schematic, partial cross-sectional side view of the dispenser of FIG. 1, detecting a user's hand that is not wearing a glove.
Figure 3:
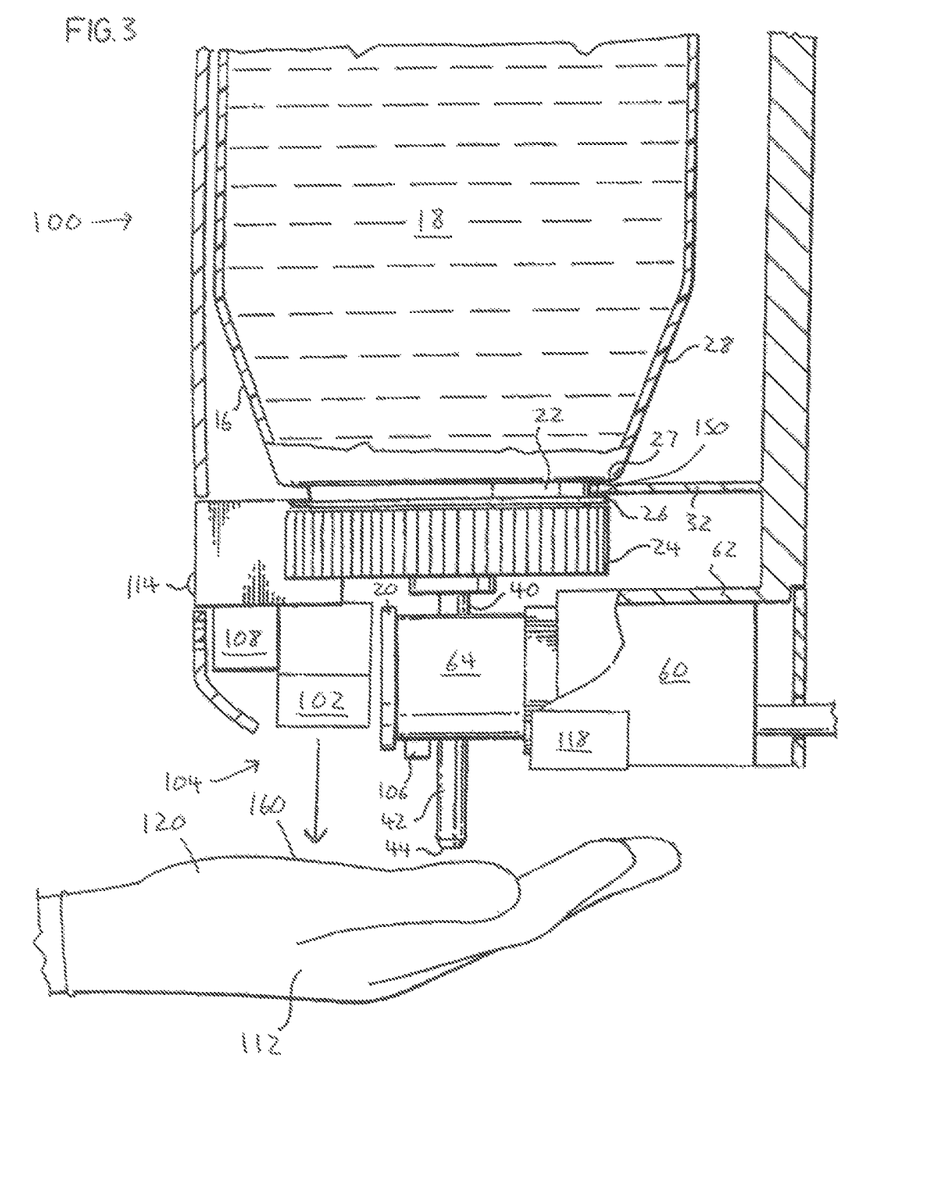
FIG. 3 is a schematic, partial cross-sectional side view of the dispenser of FIG. 1, detecting a user's hand that is wearing a glove.

FIGS. 1 to 3 show a fluid dispenser 100 in accordance with a first embodiment of the present invention. The fluid dispenser 100 corresponds to the soap dispenser taught by U.S. Pat. No. 8,245,877 to Ophardt, issued Aug. 21, 2012, which is incorporated herein by reference, modified so that the dispenser 100 is able to determine whether a user's hand 112 is wearing a glove 120.

As taught by U.S. Pat. No. 8,245,877, the dispenser 100 comprises a housing 10, a replaceable soap and pump unit 12, and a cover 14. The housing 10 is adapted to be mounted vertically as to a wall. The cover 14 is adapted to be coupled to the housing 10 to permit insertion and removal of the unit 12 preferably as in a known manner with the cover 14 hingedly connected to the housing 10. The replaceable unit 12 comprises a fluid container 16 and a pump 20.

Reference is made to FIG. 2 which shows in cross-section the container 16 filled with fluid 18. The container 16 has a cylindrical outlet neck 22 which is externally threaded at its end to threadably receive a cap 24. The neck 22 has a radially outwardly extending flange 26 disposed closely under a radially outwardly extending portion 27 of the wall 28 of the container 16 so as to present a radially extending support slot 150 therebetween. The housing 10 has a horizontally extending support plate 32 with a forwardly open U-shaped slot 34 therein sized to be complementary to the support slot 150 such that the support plate 32 can be received in the support slot 150 and support the weight of the container 16 and locate the container 16 in a desired position.

The cap 24 opens into a feed tube 40. Fluid 18 is conducted via feed tube 40 to pump 20 and then from pump 20 via an exit tube 42 out a dispensing outlet 44.

A motor 60 is mounted in a motor casing 62 in the housing 10 carrying a forwardly opening socket 64 which is sized to removably receive the pump 20 therein for operative coupling of the motor 60 to drive the pump 20.

A control mechanism 104 is provided to control operation of the dispenser 100. The control mechanism 104 includes a glove sensor 102, a hand sensor 106, a user sensor 114, and a processor 108. As shown in FIG. 1, the glove sensor 102 is mounted to a side wall 110 of the housing 10, and is directed at an angle downwardly so as to face a user's hand 112 located centrally under the outlet 44. The glove sensor 102 is preferably an infrared temperature sensor which senses the surface temperature of the user's hand 112 located under the outlet 44.

The hand sensor 106 is mounted to the lower surface of the socket 64 beside the outlet 44. The hand sensor 106 is a proximity sensor which senses when the user's hand 112 is located under the outlet 44.

The user sensor 114 is mounted to one of the side walls 110 of the housing 10, and extends forwardly through an opening 116 in the cover 14. The user sensor 114 is a proximity sensor which senses when a user is standing near the front of the dispenser 100.

The processor 108 receives signals from the glove sensor 102, the hand sensor 106, and the user sensor 114, and controls the operation of the motor 60 to drive the pump 20 and dispense the fluid 18 from the outlet 44.

The dispenser 100 also includes a data storage and transmission unit 118. The data storage and transmission unit 118 records data received from the processor 108, and periodically transmits the recorded data to a hand hygiene compliance monitoring system. The data is preferably transmitted wirelessly, but may also be transmitted via a wired connection.

The dispenser 100 may be controlled by the control mechanism 104 to operate in many different manners. In one preferred manner of operation, the hand sensor 106 detects when a user's hand 112 is placed under the outlet 44, and relays this information to the processor 108. The processor 108 then activates the glove sensor 102 to take a temperature reading of an external surface 160 presented by the hand 112. The external surface 160 may, for example, be the user's skin when the user's hand 112 is not wearing a glove 120, or the exterior surface of the glove 120 when the user's hand 112 is wearing a glove 120. The temperature information is then relayed back to the processor 108, which uses the information to determine whether the user's hand 112 is wearing a glove 120. Typically, the surface temperature of a gloved hand 112, as shown in FIG. 3, is lower than the surface temperature of an ungloved hand 112, as shown in FIG. 2, because the user's body heat gets trapped inside the glove 120. To determine whether the user's hand 112 is wearing a glove 120, the processor 108 compares the measured surface temperature of the user's hand 112 to a threshold temperature. If the measured temperature is higher than the threshold temperature, then the processor 108 determines that the user's hand 112 is not wearing a glove 120. If the measured temperature is lower than the threshold temperature, then the processor 108 determines that the user's hand 112 is wearing a glove 120.

The threshold temperature may be preset or preprogrammed into the processor 108 based on known temperature ranges of user's hands 112 when gloved or ungloved. Alternatively, the threshold temperature can be calculated by the processor 108 periodically based on changing environmental factors such as the air temperature and air circulation in the room where the dispenser 100 is located.

When the processor 108 determines that the user's hand 112 is not wearing a glove 120, as shown in FIG. 2, the processor 108 sends a first activation signal to the motor 60, which causes the motor 60 to drive the pump 20 to an extent which causes the pump 20 to dispense a first allotment of fluid 18 onto the user's ungloved hand 112. The user can then use the first allotment of fluid 18 to clean, sanitize, and/or disinfect their ungloved hand 112.

When the processor 108 determines that the user's hand 112 is wearing a glove 120, as shown in FIG. 3, the processor 108 sends a second activation signal to the motor 60, which causes the motor 60 to drive the pump 20 to an extent which causes the pump 20 to dispense a second allotment of fluid 18, which is smaller than the first allotment of fluid 18, onto the user's gloved hand 112. The user can then use the second allotment of fluid 18 to clean, sanitize, and/or disinfect their gloved hand 112.

The dispenser 100 dispenses a smaller volume of fluid 18 when the user's hand 112 is determined to be wearing a glove 120 because gloves 120 typically have an outer surface that is smoother than the outer surface of a user's naked hand 112. The outer surface of a glove 120 thus requires less hand cleaning fluid 18 to clean, sanitize, and/or disinfect in comparison with a naked hand 112. By dispensing less fluid 18 when the user's hand is determined to be wearing a glove 120, the dispenser 100 can reduce the amount of fluid 18 that is wasted, thereby providing cost savings.

Together, the processor 108, the motor 60, and the pump 20 act as a fluid adjustment system that adjusts a characteristic of the allotment of fluid 18, in this case the volume of the allotment of fluid 18, based on whether the user's hand 112 is determined to be wearing a glove 120.

Preferably, the processor 108 is configured to treat a user's hand 112 as not wearing a glove 120 if there is ambiguity in the temperature reading received from the glove sensor 102. For example, if the surface temperature of the user's hand 112 falls within a range that could occur in both gloved and ungloved hands 112, the processor 108 is preferably configured to determine that the user's hand 112 is not wearing a glove 120, and control the motor 60 to dispenser the larger first allotment of fluid 18. This helps to ensure that a sufficient volume of fluid 18 is dispensed to clean the user's hand 112 in the event that the user's hand 112 is, in fact, not wearing a glove 120.

Preferably, the processor 108 is configured to determine whether the user's hand 112 is wearing a glove 120 before the fluid 18 has been dispensed onto the user's hand 112. This is because after the fluid 18 is dispensed onto the user's hand 112, the fluid 18 may temporarily decrease the surface temperature of the user's hand 112. As such, in some circumstances, temperature readings taken immediately after the fluid 18 has been dispensed could erroneously indicate that the user's hand 112 is wearing a glove 120, when the hand 112 is in fact ungloved.

The glove sensor 102 senses the surface temperature of the user's hand 112 when the user's hand 112 is first placed under the outlet 44, before an allotment of fluid 18 is dispensed. As such, the initial temperature reading reflects the temperature of the user's hand 112 before any fluid 18 has been dispensed thereon, and would generally be expected to accurately reflect whether the user's hand 112 is wearing a glove 120. However, should the same user immediately place his or her hands under the outlet 44 again to receive an additional allotment of fluid 18, there is a risk that the surface temperature of the user's hand 112 could have been sufficiently lowered by the fluid 18 to cause the processor 108 to come to an erroneous determination as to whether the user's hand 112 is wearing a glove 120. To avoid this possibility, the processor 108 is optionally configured to make an initial determination of whether the user's hand 112 is wearing a glove 120, and then to wait until a predetermined time period has passed before making a subsequent determination as to whether the user's hand 112, or a subsequent user's hand 112, is wearing a glove 120. The predetermined time period is preferably selected based on the known or estimated average amount of time that a user interacts with the fluid dispenser 100, and preferably has a short enough duration that the predetermined time period will normally have ended before a subsequent user is able to place his or her hands 112 under the outlet 44. Once the predetermined time period has ended, the processor 108 is preferably configured to make a new determination of whether the user's hand 112 is wearing a glove 120 when the user's hand 112 is detected under the outlet 44 by the hand sensor 106.

Alternatively, the processor 108 may optionally be configured to determine, based on data received from the user sensor 114, when a user has moved in front of the dispenser 100 and when the user has moved away from the dispenser 100, and to wait until the user has moved away from the dispenser 100 before making a subsequent determination as to whether the user's hand 112, or a subsequent user's hand 112, is wearing a glove 120. In particular, the processor 108 is preferably configured to determine whether the user's hand 112 is wearing a glove 120 only when the user first puts his or her hand 112 under the outlet 44, relying on this initial determination for each subsequent dispensing of fluid 18 while the user remains standing in front of the dispenser 100. Once the user has moved away from the dispenser 100, as detected by the user sensor 114, the processor 108 is preferably configured to make a new determination as to whether the user's hand 112 is wearing a glove 120 when a subsequent user moves in front of the dispenser 100 and places his or her hand 112 under the outlet 44.

Preferably, the processor 108 sends data to the data storage and transmission unit 118 that reflects the use of the dispenser 100, including for example the number of times that the dispenser 100 has dispensed fluid 18, and whether the user's hand 112 was determined to be wearing a glove 120 or not wearing a glove 120 each time fluid 18 was dispensed. This information can then be stored locally on the data storage and transmission unit 118, or preferably is transmitted to a hand hygiene compliance monitoring system. The monitoring system can then process the data to determine whether the users of the dispenser 100 are following proper hand hygiene protocols, including the frequency of hand cleaning, and the wearing of gloves 120. The information can also be used to, for example, keep track of the volume of fluid 18 that has been dispensed, so that the dispenser 100 can be refilled or replaced when needed.

Figure 4:
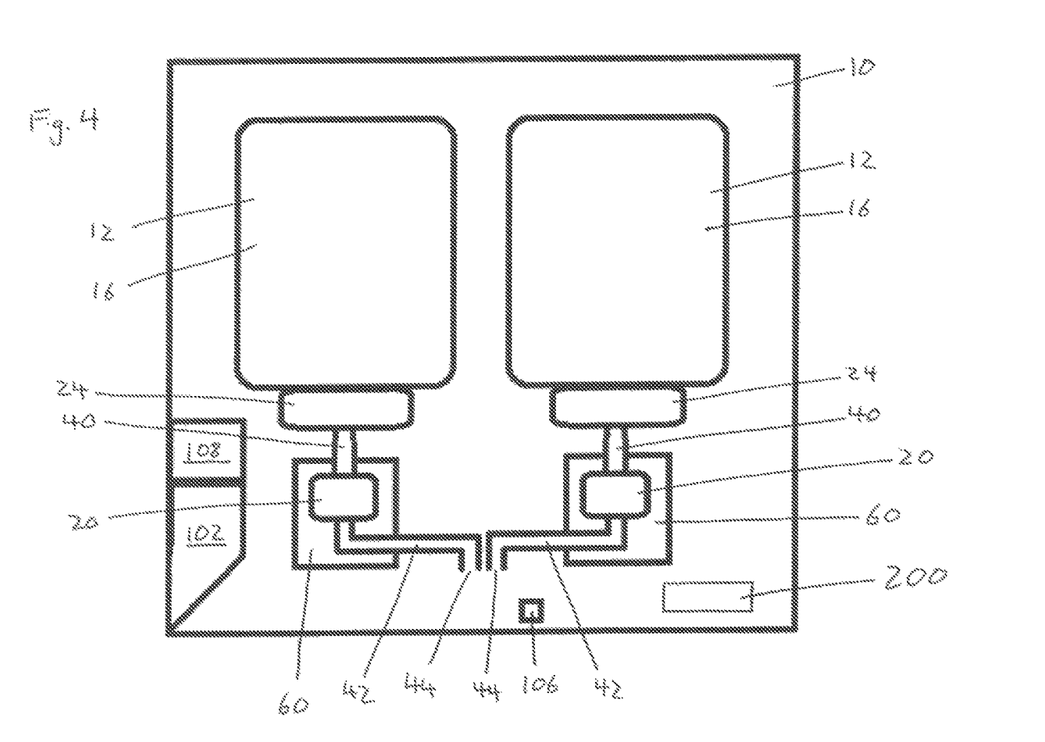
FIG. 4 is a schematic front view of a dispenser in accordance with a second embodiment of the invention.

Reference is now made to FIG. 4, which schematically shows a fluid dispenser 100 in accordance with a second preferred embodiment of the invention. The dispenser 100 shown in FIG. 4 is generally similar to the dispenser 100 shown in FIGS. 1 to 3, but is adapted to adjust the composition of the allotment of fluid 18, rather than its volume, based on whether the user's hand is determined to be wearing a glove 120. Like numerals are used to denote like components.

As shown in FIG. 4, the dispenser 100 in accordance with the second embodiment of the invention includes two separate containers 16 that contain fluids 18 having different compositions. Each container 16 has its own pump 20, and each pump 20 is operatively connected to its own motor 60. An exit tube 42 extends from each pump 20 towards the center of the dispenser 100, with each exit tube 42 having a downwardly directed dispensing outlet 44. The two dispensing outlets 44 are positioned adjacent to each other so that a user's hand 112 can be positioned below both outlets 44 simultaneously for receiving fluid 18 from either outlet 44.

The dispenser 100 shown in FIG. 4 also includes a glove sensor 102, a hand sensor 106, and a processor 108. The glove sensor 102 is angled downwardly so as to face a user's hand 112 located centrally under the outlets 44. The glove sensor 102 is preferably an infrared temperature sensor which senses the surface temperature of the user's hand 112 located under the outlets 44, similarly to the embodiment shown in FIGS. 1 to 3.

The hand sensor 106 is mounted to the housing 10 near the outlets 44. The hand sensor 106 is a proximity sensor which senses when the user's hand 112 is located under the outlets 44.

The processor 108 receives signals from the glove sensor 102 and the hand sensor 106, and controls the operation of the motors 60 to drive the pumps 20 and dispense the fluid 18 from the outlets 44.

As in the embodiment shown in FIGS. 1 to 3, in the embodiment shown in FIG. 4 the processor 108 is configured to determine whether a user's hand 112 placed under the outlets 44 is wearing a glove 120, using temperature readings provided by the glove sensor 102.

When the processor 108 determines that the user's hand 112 is not wearing a glove 120, the processor 108 sends an activation signal to a first one of the motors 60, which causes the motor 60 to drive a first one of the pumps 20 to dispense an allotment of fluid 18 from a first one of the containers 16 onto the user's ungloved hand 112. The user can then use the allotment of fluid 18 to clean, sanitize, and/or disinfect their ungloved hand 112.

When the processor 108 determines that the user's hand 112 is wearing a glove 120, the processor 108 sends an activation signal to a second one of the motors 60, which causes the motor 60 to drive a second one of the pumps 20 to dispense an allotment of fluid 18 from a second one of the containers 16 onto the user's gloved hand 112. The user can then use the allotment of fluid 18 to clean, sanitize, and/or disinfect their gloved hand 112.

By dispensing fluid 18 from a different container 16 depending on whether the user's hand 112 is determined to be wearing a glove 120, it is possible to vary the composition of the fluid 18 to best suit the cleaning of gloved or ungloved hands 112. For example, the fluid 18 that is dispensed when the user's hand 112 is determined to be wearing a glove 120 could incorporate a compound that is very effective at cleaning gloved hands 112, but is too harsh to be applied directly to a user's skin. The fluid 18 that is dispensed when the user's hand 112 is determined to not be wearing a glove 120 could likewise incorporate a compound that is effective at cleaning bare hands 112, but cannot be applied to gloved hands 112 because the compound reacts with or degrades the gloves 120.

The dispenser 100 could be adapted to include one, two, or more containers 16, with each container 16 containing a different fluid 18, and could be configured to dispense fluid 18 from any combination of one, two, or more of the containers 16. The dispenser 100 could also be adapted to vary the volume of fluid 18 dispensed from each container 16, depending on whether the user's hand 112 is determined to be wearing a glove 120. For example, the dispenser 100 could include a first container 16 that contains water and a second container 16 that contains concentrated alcohol, both of which are dispensed when the dispenser 100 is activated, but with the proportion of water to alcohol varying depending on whether the user's hand 112 is determined to be wearing a glove 120. The dispenser 100 could also be configured to dispense fluid 18 from one of the containers 16 with every activation, but to only dispense fluid 18 from another one of the containers 16 when the user's hand 112 is determined to be wearing a glove 120, or when the user's hand 112 is determined to not be wearing a glove 120.

The dispenser 100 could also be configured to dispense fluid 18 only when the user's hand 112 is determined to be wearing a glove 120, or to dispense fluid 18 only when the user's hand 112 is determined to not be wearing a glove 120. This may be advantageous, for example, if the fluid 18 that is dispensed by the dispenser 100 is too harsh to be applied to a user's skin, or if it reacts with or degrades gloves 120.

Optionally, the dispenser 100 incorporates a communication device 200, as shown schematically in FIG. 4, such as an electronic display or speaker. The communication device 200 can be used to provide a user with information about the operation of the dispenser 100. For example, if a user places an ungloved hand 112 under the fluid outlet 44 and the dispenser 100 is configured to dispense fluid 18 only when the user's hand 112 is determined to be wearing a glove 120, the communication device 200 can be used to notify the user that gloves 120 are required. The communication device 200 may, for example, be configured to display a warning signal indicating that gloves 120 must be worn whenever an ungloved hand 112 is detected under the fluid outlet 44. This can help the user to safely operate the dispenser 100, and prevent the user from erroneously concluding that the dispenser 100 is broken when no fluid 18 is dispensed. The communication device 200 could also be used to display other information, such as the composition and amount of fluid 18 contained in each of the containers 16.

Figure 5:
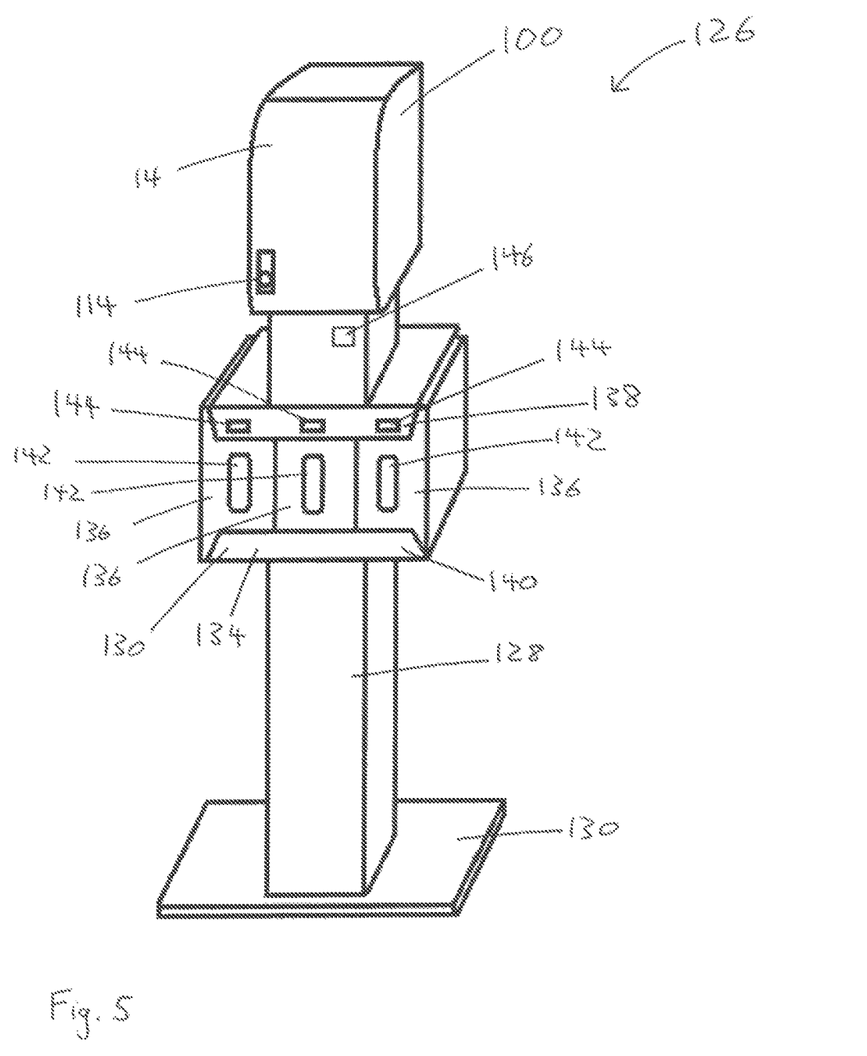
FIG. 5 is a schematic pictorial view of a hygiene station in accordance with a third embodiment of the invention.

Reference is now made to FIG. 5, which shows a hygiene station 126 in accordance with a third preferred embodiment of the invention. The hygiene station 126 has a support post 128, a glove dispenser 130, and a hand cleaning fluid dispenser 100. The hand cleaning fluid dispenser 100 corresponds identically to the fluid dispenser 100 shown in FIGS. 1 to 3. Like numerals are used to represent like components.

The support post 128 extends vertically upwards from a support base 130, which has a flat bottom surface for resting on a floor. The hand cleaning fluid dispenser 100 is mounted near the top of the support post 128, and the glove dispenser 130 is mounted near the middle of the support post 128. The glove dispenser 130 has a receptacle 134 that is preferably sized to receive three side-by-side glove boxes 136, for example for small, medium, and large sized gloves 120. In other embodiments, the receptacle 130 may be sized to hold one, two, three, or more glove boxes 136. The receptacle 134 has a top retaining member 138 that extends downwardly over the top of the glove boxes 136, and a bottom retaining member 140 that extends upwardly over the bottom of the glove boxes 136. The top retaining member 138 and the bottom retaining member 140 hold the glove boxes 136 in place in the receptacle 134, and allow a user to pull gloves 120 out from forwardly facing openings 142 in the glove boxes 136 without pulling the boxes 136 out of the receptacle 134. The left and right sides of the receptacle 134 are open, allowing the glove boxes 136 to be removed from the receptacle 134 and replaced when needed.

The top retaining member 138 is provided with three glove removal sensors 144. Each glove removal sensor 144 is positioned above the opening 142 of one of the glove boxes 136. The glove removal sensors 144 are preferably motion sensors, which detect when a glove 120 is removed from the opening 142 immediately below the sensor 144. When the glove removal sensors 144 detect that a glove 120 has been removed from one of the glove boxes 136, this information is conveyed to a station monitoring system 146.

The station monitoring system 146 also receives information from the processor 108 of the fluid dispenser 100 regarding the number and timing of fluid 18 dispensing events, as well as the presence or absence of a glove 120 on the user's hand 112 when fluid 18 is dispensed. The station monitoring system 146 records this information, or preferably transmits the information to a hygiene compliance monitoring system. The information can then be used to assess whether the users of the hygiene station 126 are complying with hand hygiene protocols in the facility where the hygiene station 126 is located.

Preferably, the station monitoring system 146 records and/or transmits information indicative of whether the fluid dispenser 100 was activated within a predetermined time period immediately preceding the removal of a glove 120 from one of the glove boxes 136. This information can be useful in that it provides an indication as to whether a user has sanitized his or her hands before putting on gloves 120, as is often required by hand hygiene protocols in healthcare facilities and other similar environments.

The station monitoring system 146 also preferably records and/or transmits information indicative of the timing, order, and number of fluid 18 dispensing events and glove 120 dispensing events during each user interaction with the hygiene station 126. For example, the station monitoring system 146 preferably receives an indication from the user sensor 114 when a user has entered a predetermined area in front of the hygiene station 126, as well as an indication when the user has left the predetermined area in front of the hygiene station 126, and links all of the recorded fluid 18 dispensing events and glove 120 dispensing events that occur during the time period while the user is in the predetermined area as corresponding to a single user interaction with the hygiene station 126. Linking all of this information together can help the hand hygiene compliance monitoring system provide a more detailed assessment of how users are interacting with the hygiene station 126, and whether they are following the proper hand hygiene protocols. By combining the dispensing of fluid 18, the dispensing of gloves 120, and the recording of fluid 18 dispensing events and glove 120 dispensing events in one place, the hygiene station 126 allows this information to be easily and accurately recorded and linked.

It will be understood that, although various features of the invention have been described with respect to one or another of the embodiments of the invention, the various features and embodiments of the invention may be combined or used in conjunction with other features and embodiments of the invention as described and illustrated herein.

The fluid dispenser 100 is not limited to the particular construction shown and described herein. For example, the dispenser 100 does not need to include a user sensor 114 or a hand sensor 106. If the dispenser 100 does not include a hand sensor 106, the dispenser 100 may be activated by, for example, the user pressing a button on the dispenser 100. A single sensor could also function as both the hand sensor 106 and the glove sensor 102. For example, an infrared temperature sensor could be used to detect when the user's hand 112 is placed under the outlet 44 by sensing the heat from the user's hand 112, thereby functioning as the hand sensor 106, and also function as the glove sensor 102 by sensing whether the temperature of the external surface 160 of the user's hand 112 falls above or below a threshold temperature.

Also, the glove sensor 102 does not necessarily need to be a temperature sensor. Rather, any type of sensor or sensors that can be used to determine whether a user's hand 112 is wearing a glove 120 could be used instead. For example, in an alternative embodiment the glove sensor 102 is provided as an optical sensor that can detect, for example, the color of the external surface 160 presented by the user's hand 112; a presence or an absence of a visual feature on the external surface 160 presented by the user's hand 112, such as a visual pattern; a reflective property of the external surface 160 presented by the user's hand 112; a light absorption property of the external surface 160 presented by the user's hand 112; and/or a relative location or distance of the external surface 160 presented from the dispenser 100. This information is then sent to the processor 108, which compares the measured characteristics of the external surface 160 presented by the user's hand 112 with known or expected characteristics of gloved and ungloved hands 112, and based on this comparison determines whether or not the user's hand 112 is wearing a glove 120.

The optical sensor may, for example, be a camera that takes an image of the external surface 160 of the user's hand 112, and sends the image to the processor 108 to be processed using image recognition software. The software may, for example, identify features such as color, contrast, and shape, and by comparing these features to the known or expected features of gloved and ungloved hands 112, determine whether the user's hand 112 is wearing a glove 120. The dispenser 100 may, for example, be configured to detect a specific brand or type of glove 120 that has a distinctive visual feature, such as a color or a printed pattern. In some embodiments of the invention, the dispenser 100 may be configured to distinguish between different types of gloves 120, for example where each type of glove 120 has a distinctive visual feature, and to control the operation of the dispenser 100 depending on which type of glove 120 is being worn. For example, the dispenser 100 could be controlled to adjust the allotment of fluid 18 based on the type of glove 120. This may be advantageous, for example, where different types of gloves 120 that are made from different materials are being used, by allowing the composition of the allotment of fluid 18 to be adjusted based on the glove material.

The glove sensor 102 could also be provided as an ultrasonic sensor/transducer, which emits a short pulse of ultrasound towards the external surface 160 presented by the user's hand 112 and records the signal reflected back from various acoustic boundaries, such as the user's skin or the exterior surface of a glove 120. The ultrasonic waves that are reflected back from the external surface 160 can be used to detect various properties of the material from which the external surface 160 is formed, such as its elasticity and density. The detected acoustic properties of the external surface 160 can be used to determine whether or not the user's hand 112 is wearing a glove 120, by comparing the detected acoustic properties of the external surface 160 with the known or expected acoustic properties of bare hands 112 versus gloved hands 112.

In some embodiments of the invention, the dispenser 100 does not include the data storage and transmission unit 118. In other embodiments, the unit 118 may only provide data storage functionality, but not data transmission, or may only provide data transmission functionality, but not data storage. The dispenser 100 also does not necessarily require the processor 108. Rather, the data generated by the glove sensor 102 could be directly transmitted to a compliance monitoring system, for example, without first being processed by a processor 108 in the dispenser 100. The dispenser 100 also does not necessarily require a fluid adjustment system that adjusts a characteristic of the allotment of fluid 18 based on whether the user's hand 112 is determined to be wearing a glove 120. Rather, the information about whether the user's hand 112 is wearing a glove 120 could be used for compliance monitoring, for example, without also being used for making adjustments to the allotment of fluid 18.

The hygiene station 126 also is not limited to the particular construction shown and described herein. For example, the hygiene station 126 need not incorporate the fluid dispenser 100 as shown in FIGS. 1 to 3, and could instead incorporate any suitable fluid dispenser 100 that dispenses fluid 18 and transmits information indicative of the number and/or timing of fluid 18 dispensing events to the station monitoring system 146. The glove dispenser 130 may also have any suitable construction, and is not limited to the particular construction shown in FIG. 5. The support base 132 could also be provided with wheels, so that the hygiene station 126 can be moved to different locations when needed.

The information indicative of the number and/or timing of fluid 18 dispensing events could be generated by any suitable method. For example, when the processor 108 sends an activation signal to the motor 60, the processor 108 could simultaneously send a signal to the data storage and transmission unit 118 indicating that fluid 18 is being dispensed. Alternatively, the dispenser 100 could incorporate additional sensors to detect when fluid 18 has been dispensed, such as sensors that detect the movement of the pump 20 or the flow of fluid 18 through the outlet 44, and the information indicative of the number and/or timing of fluid 18 dispensing events could be generated by the processor 108 based on information received from these additional sensors.

Although the fluid 18 is preferably a hand cleaning fluid, such as hand soap or hand sanitizer, the dispenser 100 could be used to dispense other fluids as well. The term "fluid" as used herein includes any flowable substance, including liquids, foams, emulsions, and dispersions.

The phrase "determined to not be wearing a glove 120" and other similar expressions as used herein are intended to mean that the dispenser 100 treats the user's hand 112 as though the user's hand 112 is not wearing a glove 120, or considers the user's hand 112 to not be wearing a glove 120. In some circumstances and in some embodiments of the invention, the dispenser 100 may consider the user's hand 112 to not be wearing a glove 120, even though the hand 112 is in fact wearing a glove 120. This may occur, for example, if the temperature of the external surface 160 presented by the user's hand 112 falls within a range that could be found in both gloved and ungloved hands 112, and the dispenser 100 treats the hand 112 as not wearing a glove 120 to ensure that a sufficient volume of fluid 18 is dispensed. The dispenser 100 of the present invention may be used in healthcare settings and other similar environments to determine whether a user, such as a medical professional, is wearing a medical or surgical glove 120. The dispenser 100 is preferably configured to detect gloves 120 that are made from any suitable material, including for example latex, nitrile rubber, polyvinyl chloride, and neoprene. The dispenser 100 may also be used to detect other types of gloves 120, including for example leather gloves 120, cloth gloves 120, chain mail gloves 120, safety gloves 120, disposable gloves 120, food service gloves 120, and rubber gloves 120.

Although this disclosure has described and illustrated certain preferred embodiments of the invention, it is to be understood that the invention is not restricted to these particular embodiments. Rather, the invention includes all embodiments which are functional or mechanical equivalents of the specific embodiments and features that have been described and illustrated herein.

We claim:

1. A method comprising:
providing a fluid dispenser having a sensor that senses a property of an external surface presented by a user's hand, and a pump mechanism that, when activated, dispenses an allotment of fluid onto the user's hand; the allotment having a volume,
using the sensor to sense the property of the external surface presented by the user's hand;
determining, based on the property of the external surface presented by the user's hand, whether the user's hand is wearing a glove,
decreasing the volume of the allotment of fluid dispensed when the user's hand is determined to be wearing a glove compared to the volume of the allotment of fluid dispensed when the user's hand is determined to not be wearing a glove.

2. The method according to claim 1, further comprising:
adjusting a characteristic of the allotment of fluid other than the volume based on whether the user's hand is determined to be wearing a glove.

3. The method according to claim 2, wherein the characteristic of the allotment of fluid other than the volume that is adjusted based on whether the user's hand is determined to be wearing a glove comprises a composition of the allotment of fluid.

4. The method according to claim 1, wherein the fluid dispenser further comprises a data storage unit and/or a data transmission unit, the method further comprising at least one of:
using the data storage unit to record information indicative of whether the user's hand is determined to be wearing a glove; and
using the data transmission unit to transmit the information indicative of whether the user's hand is determined to be wearing a glove.

5. The method according to claim 4, wherein the information indicative of whether the user's hand is determined to be wearing a glove is transmitted to a compliance monitoring system.

6. The method according to claim 1, wherein the sensor comprises at least one of: a temperature sensor, an ultrasonic sensor, and an optical sensor.

7. The method according to claim 1, wherein the sensor comprises an infrared sensor that senses a temperature of the external surface presented by the user's hand, the method further comprising:
using the infrared sensor to sense whether the external surface presented by the user's hand is above or below a threshold temperature;
determining that the user's hand is wearing a glove if the temperature of the external surface presented by the user's hand is below the threshold temperature; and
determining that the user's hand is not wearing a glove if the temperature of the external surface presented by the user's hand is above the threshold temperature.

8. The method according to claim 7, wherein the fluid dispenser determines whether the user's hand is wearing a glove before the allotment of fluid is dispensed onto the user's hand; and
wherein the fluid dispenser waits until at least one of:
(a) a predetermined time period has passed; and
(b) the user has moved away from the fluid dispenser;
before making a subsequent determination of whether the user's hand, or a subsequent user's hand, is wearing a glove.

9. The method according to claim 1, wherein the sensor comprises an optical sensor, and the optical sensor detects at least one of:
- a color of the external surface presented by the user's hand;
- a presence or an absence of a predetermined visual feature on the external surface presented by the user's hand;
- a reflective property of the external surface presented by the user's hand; and
- a light absorption property of the external surface presented by the user's hand.

10. The method according to claim 1, wherein the fluid is a hand cleaning fluid, the method further comprising:
dispensing the allotment of fluid onto the user's hand.

11. The method according to claim 1, wherein the fluid is a hand cleaning fluid; and
wherein the fluid dispenser further comprises a data transmission unit, the method further comprising:
dispensing the allotment of fluid onto the user's hand; and
using the data transmission unit to transmit information indicative of whether the user's hand is determined to be wearing a glove to a compliance monitoring system.

12. The method according to claim 11, wherein the sensor comprises an infrared sensor that senses a temperature of the external surface presented by the user's hand, the method further comprising:
using the infrared sensor to sense whether the external surface presented by the user's hand is above or below a threshold temperature;
determining that the user's hand is wearing a glove if the temperature of the external surface presented by the user's hand is below the threshold temperature; and
determining that the user's hand is not wearing a glove if the temperature of the external surface presented by the user's hand is above the threshold temperature.

13. A fluid dispenser comprising:
a pump mechanism that, when activated, dispenses an allotment of fluid onto a user's hand;
the allotment having a volume,
a sensor that senses a property of an external surface presented by the user's hand; and
a processor that determines, based on the property of the external surface presented by the user's hand, whether the user's hand is wearing a glove,
a fluid adjustment system that adjusts the volume of the allotment of fluid dispensed by the pump mechanism based on whether the user's hand is determined to be wearing a glove,
the fluid adjustment system decreasing the volume of the allotment of fluid dispensed when the user's hand is determined to be wearing a glove compared to the volume of the allotment dispensed when the user's hand is determined to not be wearing a glove.

14. The fluid dispenser according to claim 13, further comprising a data transmission unit that transmits information indicative of whether the user's hand is determined to be wearing a glove to a compliance monitoring system.

15. The fluid dispenser according to claim 13 wherein:
the sensor comprises an infrared sensor that senses a temperature of the external surface presented by the user's hand,
the processor using the infrared sensor to sense whether the external surface presented by the user's hand is above or below a threshold temperature;
the processor determining that the user's hand is wearing a glove if the temperature of the external surface presented by the user's hand is below the threshold temperature; and
the processor determining that the user's hand is not wearing a glove if the temperature of the external surface presented by the user's hand is above the threshold temperature.

16. The fluid dispenser according to claim 13 including a user sensor which senses when a user is standing near a front of the dispenser,
the processer determines whether the user's hand is wearing a glove before the allotment of fluid is dispensed onto the user's hand;
wherein the processor controls operation of the pump mechanism to wait until at least one of:
(a) a predetermined time period has passed; and
(b) a determination is made the user has moved away from the fluid dispenser based on input from the user sensor;
before making a subsequent determination of whether the user's hand, or a subsequent user's hand, is wearing a glove.

17. A method comprising:
providing a fluid dispenser having a glove sensor that senses a property of an external surface presented by a users hand, and a pump mechanism that, when activated, dispenses an allotment of fluid onto the users hand; the allotment having a volume,
using the glove sensor to sense the property of the external surface presented by the user's hand; and
determining, based on the property of the external surface presented by the user's hand, before the allotment of fluid is dispensed onto the user's hand, whether the user's hand is wearing a glove,
wherein the fluid dispenser waits until at least one of:
(a) a predetermined time period has passed; and
(b) the user has moved away from the fluid dispenser;
before making a subsequent determination of whether the user's hand, or a subsequent user's hand, is wearing a glove.

18. The method according to claim 17, wherein the glove sensor comprises an infrared sensor that senses a temperature of the external surface presented by the user's hand, the method further comprising:
using the infrared sensor to sense whether the external surface presented by the user's hand is above or below a threshold temperature;
determining that the user's hand is wearing a glove if the temperature of the external surface presented by the user's hand is below the threshold temperature; and
determining that the user's hand is not wearing a glove if the temperature of the external surface presented by the user's hand is above the threshold temperature.

19. The method according to claim 17 including:
providing the dispenser with a user sensor which senses when a user is standing near a front of the dispenser,
determining whether the user has moved away from the fluid dispenser based on input from the user sensor.

20. A fluid dispenser comprising:
a pump mechanism that, when activated, dispenses an allotment of fluid onto a user's hand;
the allotment having a volume,
a glove sensor that senses a property of an external surface presented by the user's hand; and
a processor that determines, based on the property of the external surface presented by the user's hand, whether the user's hand is wearing a glove, a user sensor which senses when a user is standing near a front of the dispenser, wherein the processer determines whether the user's hand is wearing a glove before the allotment of fluid is dispensed onto the user's hand; and the processor controls operation of the pump mechanism to wait until at least one of:

(a) a predetermined time period has passed; and (b) a determination is made the user has moved away from the fluid dispenser based on input from the user sensor;

before making a subsequent determination of whether the user's hand, or a subsequent user's hand, is wearing a glove.

* * * * *